United States Patent [19]

Boros et al.

[11] Patent Number: 4,703,012

[45] Date of Patent: Oct. 27, 1987

[54] HIGH COPY-NUMBER PLASMID VECTORS, PRODUCTION AND USE THEREOF

[75] Inventors: Imre Boros; Pal Venetianer; György Posfai, all of Szeged, Hungary

[73] Assignee: Richter Gedeon Vegyeszeti Gyar R.T., Budapest, Hungary

[21] Appl. No.: 651,679

[22] Filed: Sep. 17, 1984

[30] Foreign Application Priority Data

Sep. 16, 1983 [HU] Hungary .................. 3212/83

[51] Int. Cl.$^4$ .............. C12P 19/34; C12N 15/00; C12N 7/00; C12N 1/20
[52] U.S. Cl. ........................... 435/320; 435/91; 435/172.3; 435/253; 935/39; 935/42
[58] Field of Search .............. 435/172.3, 317, 253; 935/42, 73

[56] References Cited

FOREIGN PATENT DOCUMENTS

| | | |
|---|---|---|
| 0003062 | 7/1979 | European Pat. Off. |
| 0013830 | 8/1980 | European Pat. Off. |
| 0060045 | 9/1982 | European Pat. Off. |
| 0104061 | 3/1984 | European Pat. Off. |
| 0126166 | 11/1984 | European Pat. Off. |

OTHER PUBLICATIONS

Chem. Abstracts, vol. 91, No. 25, Dec. 17, 1979, 207243f.
Proc. Nat. Acad. Sci., vol. 79, pp. 3570–3574, Jun. 1982, Wong et al., Temperature-Sensitive Copy Number Mutants of ColEl are Located in an Untranslated Region of the Plasmid Genome.
*Nature,* vol. 283, Jan. 10, 1980, pp. 216–218, MacMillan Journals Ltd.; A. J. Twigg et al, Trans-Complementable Copy-number Mutants of Plasmid ColEl.
Molecular and General Genetics, vol. 188, 1982, pp. 338–344, M. J. J. Hakkaart et al., Maintenance of the Bacteriocinogenic Plasmid Clo DF13 in Escherichia Coli Cells.
Peden, K. W. C. Gene 22, pp. 277–280 (1983).
Stanier et al. in *Microbiol World,* 4th Ed. Prentice-Hall, Inc., 1976, pp. 413–414 and 441–444.
Lacatenu et al., Nature, 294: 623–626, 1981 (Dec.).
Donbora et al., P.N.A.S. USA, 78(8): 4699–4703, 1981 (Aug.).
Stougaard et al., P.N.A.S. USA, 78(10): 6008–6012, 1981 (Oct.).

*Primary Examiner*—Thomas G. Wiseman
*Assistant Examiner*—Thomas D. Mays
*Attorney, Agent, or Firm*—Karl F. Ross; Herbert Dubno; Jonathan Myers

[57] ABSTRACT

Plasmid vectors and a process for the preparation thereof are disclosed having the same replication region as pBR322, but which have a substantially higher copy number per cell. The plasmid vectors contain a G→T point mutation at base pair 3074 of the pBR322 sequence which holds back synthesis of the repressor of plasmid replication, and also contain either no tetracycline resistance gene or the tetracycline resistance gene in an inactivated or weakened state.

12 Claims, 7 Drawing Figures

HIGH COPY-NUMBER PLASMID VECTORS, PRODUCTION AND USE THEREOF

This invention relates to plasmid vectors as well as to the production and use thereof; more particularly, it relates to plasmid vectors which have a high copy number and to their production and use.

The so-called gene manipulation technique or, in other words, genetic engineering is becoming more and more important in the production of medically useful products. According to a preferred version of this technique the gene section coding for the production of the desired pharmaceutically active product is inserted into a vector, e.g. plasmid, to provide a recombinant "hybrid" plasmid molecule, which is then used to transform a suitable microorganism. The plasmid is then replicated together with the bacterial host, and the inserted gene is functioning. The amount of the gene products depends on the intensity of the translation and transcription, on the decomposition of the gene product inside the cell and on the copy-number of the gene, i.e. of the plasmid carrying the gene. Accordingly, if one succeeds in increasing the copy number of a plasmid in a cell, a substantial increase in the amount of gene products can be obtained through the increase of the copy number of the foreign gene. (As to the gene manipulation technique see e.g. U.S. Pat. No. 4,237,224.)

The object of the present invention is to provide plasmid vectors which have a substantially higher copy number per cell than the known and widely used plasmids.

In scientific research and industry a large variety of different, generally artifically constructed plasmid vectors is used. One of the most widely used plasmids is pBR322, which was first constructed by Boyer et al. [Gene, 2, 95–113 (1977)]. Since up to the present we have the most exhaustive scientific information about this plasmid, and most of the gene cloning procedures have been carried out with this plasmid or its derivatives, we used this substance as starting material in our experiments. The structure of pBR322 was determined by Sutcliffe [CSH Symp. Quant. Biol. 43, 77–90 (1979)] and is illustrated in FIG. 1. This plasmid has a molecular length of 4362 bp. The replication of the plasmid starts at the nucleotide 2536 in counter-clockwise direction and its copy number per cell is generally between 20 and 50. The copy number is controlled by a complicated regulating mechanism [Plasmid 9, 1, (1983)]. The fragment between the nucleotides 2978 and 3081 is responsible for the synthesis of a low molecular weight RNA, which does not code for any protein and which is transcribed in a clockwise direction with a relatively high intensity. This RNA of low molecular weight is the negative regulator (repressor) of plasmid replication.

The invention is based on the recognition that the copy number of the plasmid can substantially be increased by providing in the gene section responsible for the production of the repressor of plasmid replication a mutation which impairs this function of said gene section.

In our laboratory the first high copynumber plasmid (pHCl) was isolated as a product of spontaneous mutation, in an experiment carried out with amp$^r$, tet$^s$ phenotype plasmids containing a foreign DNA between the EcoRI and BamHI cleaving sites of the plasmid pBR322, during the analysis of a pool of recombinants consisting of about 5000 independent plasmids. From the bacterium cells containing the plasmid pHCl about 20–30 times more plasmid DNA could be isolated without amplification than from the clones containing other recombinant molecules with similar structure. The repeated retransformation of the plasmid pHCl, using E.coli HB101 (pro$^-$, leu$^-$, thi$^-$, lac$^-$, str$^-$, r$^-$m$^-$rndol$^-$, recA$^-$) [Boyer, H. W. et al.: J. Mol. Biol. 41, 459–472 (1979)], C600 ($r_k^-$, $m_k^-$, thi$^-$, thr$^-$, leu$^-$, lac$^-$) [Boyer, H. W. et al., ibid.], ED8800 (supE, supF, hsdS$^-$, met$^-$, lacZM15, recA56) [Murray, N. E. et al.: Mol. gen. Genet. 150, 53–61 (1977)] host cells each time resulted in the production of amp$^r$, tet$^s$ clones containing a high amount of plasmid. As a reason for the increased copy number, which was about 20–30 times higher than that of the pBR plasmids, we supposed a heritable change in the plasmid DNA.

Identification of the mutation responsible for high copy number

The plasmid pHCl was digested with restriction endonucleases EcoRI and PvuII, and then the single-stranded ends were filled with the Klenow sub-fragment of the DNA polymeraseI enzyme, in the presence of dNTP substrates. The thus-produced DNA molecules with blunt ends were circularized with a polynucleotide ligase enzyme and transformed into HB101 cells. From the colonies grown on an ampicillin-containing medium plasmid DNA was isolated and the DNA samples, which could be isolated in a high amount, were analysed by agarose and polyacrylamide gel electrophoresis, after digestion with restriction endonucleasesEcoRI, PvuII and BspRI. The plasmid pHC81 (FIG. 2) chosen for further investigation could not be digested with the enzyme PvuII and was linearized with EcoRI. On the basis of the total molecular weight of the plasmid (2.3 kb) and the size of the fragments obtained by digestion with BspRI (587, 457, 434, 267, 240, 80 . . . bp) it was established that the plasmid pHC81 contained the section between the nucleotides 2069 and 2 of the plasmid pBR322 with a mutation responsible for the high copy number. This mutation cannot be detected on the basis of the size of any of the fragments produced by the enzymes employed. To locate the mutation, the 1030 bp DNA fragment obtained by the digestion of pHC81 with the restriction endonucleases PstI and TaqI, the 780 bp DNA fragment obtained by the digestion of pBR322 with enzymes PstI and ClaI and the 218 bp DNA fragment obtained by the digestion of pBR329 with the enzyme TaqI were isolated. The three DNA fragments were mixed in equimolar proportion, they were ligated with a polynucleotide ligase and then HB101 cells were transformed with the ligate. From the single clones grown on amplicillin-containing medium plasmid DNA was isolated. These plasmids exhibited the high copy-number phenotype. By digesting the plasmid DNA-s with restriction endonucleases it was established that they were produced by the linkage of three well distinguishable fragments of different origin; in the obtained plasmids the proximal part of the β-lactamase gene was of pBR322 origin, the region containing the replication origo was derived from the plasmid pBR329 and the fragment isolated from pHC81 contained in addition to the distal part of the β-lactamase gene also the mutation resulting in the high copy number. It was, therefore, concluded that the mutation was formed between the nucleotides 2573 (TaqI) and 3612 (PstI) of the DNA of plasmid pBR322.

The nucleotide sequence of this region was determined and compared with the known pBR322 sequence. This comparison showed that a G→T transition(G=desoxyguanyl, T=thimidyl) took place at the nucleotide 3074, which corresponds to a C→A transition in the complementary DNA strand (C=desoxycytosyl, A=-desoxyadenyl).

As a result of the ensued point mutation the termination of the transcription of the repressor RNA is damaged and an RNA of higher molecular weight is synthetized which cannot function as a repressor of replication any more. The termination of the repressor function results in the higher copy number. By this spontaneous point mutation, which can be produced also intentionally, the copy number of the plasmid per cell could be increased about 20-30-times ($\approx$1000) in relation to the original value. By this point mutation the copy number of any plasmid having the same replication region as pBR322 can substantially be increased.

It has been found, however, that the original plasmid pBR322 containing a G→T point mutation is not viable any more. Namely, owing to the high copy number, on the genes of the plasmid which determine the antibiotic resistance—$Ap^r$=$\beta$-lactamese, $Tc^r$→=membrane protein(s), the synthesis of both proteins is increased, and the latter one (membrane protein responsible for tetracycline resistance) is lethal for the cell in the increased quantity. The same problem is observed in case of any high copy-number derivative of plasmid pBR322 which contains the original tetracycline resistance gene in an unaltered form.

In our previous experiments we did not have to face this problem since we used plasmids in which foreign DNA fragments had been cloned between the sites BamHI and EcoRI of the plasmid pBR322, and in this way the tetracycline resistance gene was inactivated. Accordingly, in order to obtain a viable high copy-number plasmid, pBR322 or a derivative thereof having the same replication region has to be modified by inactivating or repressing the function of the tetracycline resistance gene.

Therefore, according to a preferred embodiment of the invention there are provided new plasmids, derived from pBR322 or derivatives thereof containing the same replication region, characterized in that they do not contain a tetracycline-resistance gene, or contain it in an inactivated form or modified form with moderated function, and they contain a point mutation modifying the repressor production on the gene section coding the repressor RNA.

According to a more preferred embodiment of the invention in the plasmid DNA pBR322 or a derivative thereof having the same replication region, in the position 3074 (following the numbering of pBR322) the base pair GC is replaced by TA by controlled point mutation or by replacing a section containing this mutation in a pHC plasmid, to be described hereinafter, with a section of the desired plasmid which is, apart from this mutation, identical.

As described above, if pBR322 or a suitable derivative thereof is used as a model substance, the GC→TA point mutation has to be produced on a derivative of the starting plasmid in which the tetracycline resistance gene is entirely lacking or its function is inactivated or repressed. In this context represseion means that the gene coding for the production of the membrane protein responsible for tetracycline resistance is altered to direct a decreased protein production. According to a preferred version, the DNA responsible for tetracycline resistance or the total section up to the replication origo of pBR322 is eliminated and, if desired, is replaced by a polylinker of synthetic origin, whereby, owing to the additional restriction endonuclease digestion sites inserted into the plasmid, the application possibilities of the plasmids obtained are substantially extended.

Figure 1:
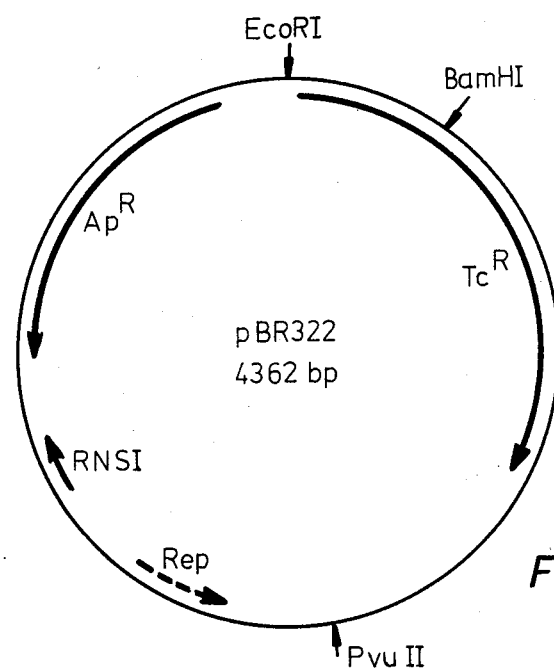
FIG. 1 is a schematic drawing of plasmid pBR322 which is the prior art.
Figure 2:
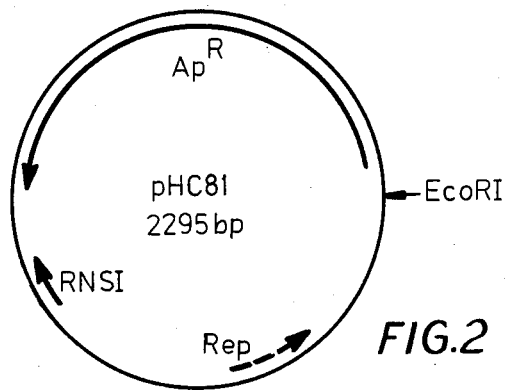
FIG. 2 is a schematic drawing of pHC81, a new plasmid vector.

Construction of plasmids pHC314, pHC312 and pHC624

During the further transformation of the plasmids obtained in the experiments described hereinabove, polylinkers were inserted into the pHC81 plasmid in order to prepare vectors suitable for the insertion of DNA fragments formed with various restriction endonucleases. The DNA of plasmid pHC81 linearized with the endonuclease EcoRI and dephosphorylated with bacterial alkaline phosphatase was ligated with plasmid DNA fragments [Seed, B.: Nucleic Acid Research 11, 2427–2446 (1983)], and E. coli HB101 cells were transformed with the ligate. From the Ap resistent bacterial colonies plasmid DNA was isolated and analysed by gel electrophoresis, after digesting with EcoRI and PstI restriction endonucleases. For further investigations the plasmid which could be cleaved to 2300 and 110 bp fragments by EcoRI, aand to 1580 and 820 bp fragments by PstI was selected (pHC 314, FIG. 3.). From this plasmid pHC312 containing only one EcoRI site was constructed as follows: The plasmid was digested with the restriction endonuclease BamHI, and the linear molecule obtained was partially digested with a HinfI enzyme. The DNA fragments were separated in a 1.2% agarose gel, and the 2010 bp fragment was isolated. The molecule ends containing single-stranded sections due to the digestion with enzymes BamHI and HinfI were converted to blunt ends with the Klenow subfragment of the enzyme DNA polymeraseI and then recircularized with $T_4$ induced polynucleotide ligase. The ligated DNA was transformed into HB101 cells, and single clones were isolated. For further operations the plasmid pHC312 which could not be cleaved with endonuclease BamHI but could be linearized with EcoRI and produced fragments 1495 bp and 516 bp upon digestion with HinfI was selected (FIG. 4). To produce a high copy-number vector suitable for cloning DNA fragments with blunt ends, plasmid pHC312 was digested with restriction endonucleases EcoRI and HindIII, and the 1980 bp fragment was isolated from agarose gel. This fragment was then admixed with the DNA of plasmid πAN7 [Seed, B.: Nucleic Acids Research, 11, 2427–2446 (1983)] digested with enzymes EcoRI and HindIII, and the molecules were linked with polynucleotide ligase. *E. coli* HB101 cells were transformed with the ligated plasmid, and from single, Ap resistant bacterium clones plasmid DNA was isolated. The plasmid DNA prepared in this way (pHC624, FIG. 5) has no ClaI site but, unlike plasmid pHC312, can be linearized with restriction endonucleases SmaI, SalI and BamHI.

Determination of the copy number of plasmids

Relative copy number

To determine the relative copy number of pHC plasmids, *E. coli* HB101 cultures containing plasmids of different size derived from recombinant pBR322 and high copy-number derivatives of the same size were grown until identical cell density. From identical amounts of the suspensions obtained, without amplification, plasmid DNA was isolated following the technique described by Birnboim and Doly [Nucleic Acids Res. 7, 1513-1523 (1979)]. Samples taken from the DNA preparates were subjected to electrophoresis on agarose gel, in 5, 10, 15, 20, 25, 30, 40 and 50-times dilutions, respectively. The high copy-number plasmids and their normal copynumber pairs (having the same molecular weight) were examined simultaneously. Experimental results showed that the copy number of pHC plasmids was about 20 to 30-times higher than that of the corresponding "normal copy-number" pBR322 derivatives.

Absolute copy number

The absolute copy number of pHC plasmids was determined by labelling the DNA of the cells containing the plasmids in vivo and measuring the ratio of radioactivity in the separated plasmid DNA and in the chromosomal DNA. By this method the copy number of plasmids having the same size as pHC314 (Mw=$1.6 \cdot 10^6$ d) was found to be about 1000/per cell (molecular weight of chromosome=$2 \cdot 10^9$ d). 60 to 65% of the total DNA content of the cell was plasmid DNA. For in vivo labelling of the DNA the cells containing the plasmids were cultivated on an M9 culture medium supplemented with the following components: 0.5% of casamino acid (Difco), 0.5% of glucose, 1 $\mu$g/ml. of vitamin $B_1$, 1 mmole of $MgSO_4$, 2 $\mu$g/ml. of thymidine, 250 $\mu$g/ml. of adenosine and 0.4 mBq/ml. of [$^3$H]-thymidine [888tBq/mmole, Chemapol, Prag].

The plasmid-containing cells were digested according to Womble et al. [J. Bacteriol, 130 (1977) 148-153]. The chromosomal and plasmid DNA were separated from each other by ethidium bromide/cesium chloride equilibrium density gradient centrifugation of the cell lysate derived from a bacterium suspension grown to 2 ml. ($OD_{550}$=4-5/45000 rpm, Beckman Type 65 rotor, 40 hours, 20° C.).

Figure 6:
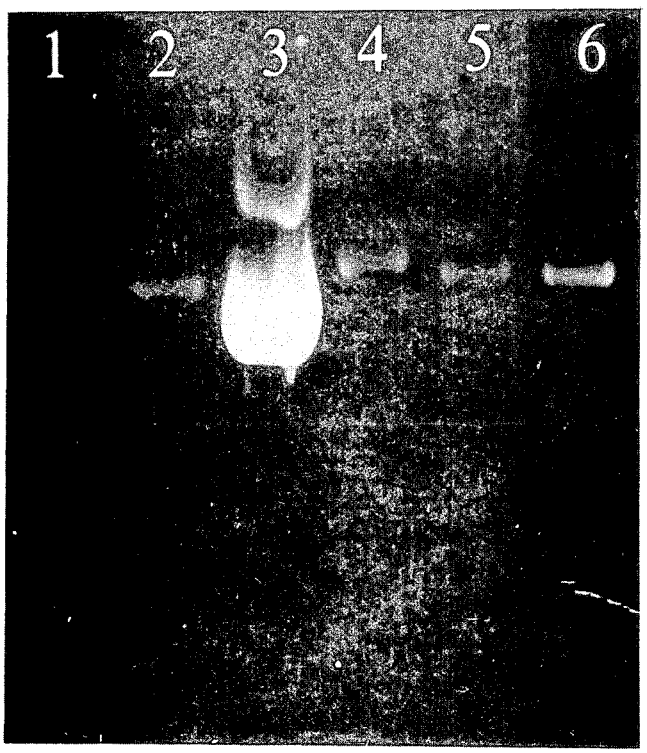
FIG. 6 is an electrophoresis pattern showing the behaviour of pBR322 and related plasmids after separation by ethidium bromide/agarose gel electrophoresis.
Figure 7:
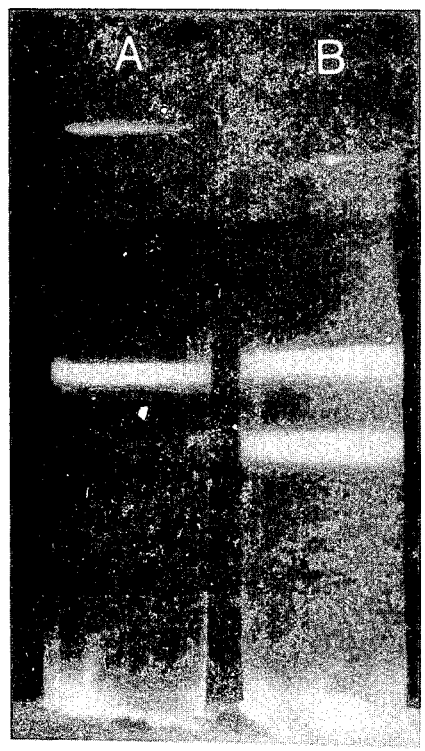
FIG. 7 is another electrophoresis pattern.

The increased copy number is illustrated on FIGS. 6 and 7.

On FIG. 6 spots corresponding to Ap$^r$, Tc$^s$ recombinant plasmid DNA-s of pBR322 origin are shown after separation by ethidium bromide/agarose gel electrophoresis. All samples were prepared by the same technique, from the same amount of plasmid-containing HB101 cells [Birnboim and Doly, Nucleic Acids Res. 7, 1513-1523 (1979)]. Samples 1-2 and 4-6 are recombinant plasmids containing a 1.5 to 2.0 kb foreign DNA between the cleaving sites EcoRI and BamHI of plasmid pBR322. Sample 3 is a plasmid of the same size, which contains the mutation responsible for high copy number (pHCl).

On FIG. 7 spots of the DNA of *E. coli* HB101 cells containing the plasmid p715 (sample A) and the plasmid pHC314 (sample B) are shown after separation by ethidium bromide/cesium chloride gradient centrifugation. (The plasmid p715 has the same structure as pHC314, except for the mutation responsible for the high copy number.) The picture was taken after separation of the plasmid and chromosomal DNA by centrifugation, under u.v. illumination of the centrifuge tube containing the DNA. As it is clearly shown in the picture, in the DNA obtained from the cells containing the normal copy-number plasmid (sample A) the plasmid-containing lower stripe is almost entirely lacking. On the other hand, the pHC314 plasmid DNA obtained from the same amount of cells by the sme technique forms a broad stripe below the stripe containing the chromosomal DNA, due to the substantially increased copy number of the plasmid.

In the experiments the following materials and techniques were used:

Bacterium strains and plasmids:

pBR322 amp$^r$, tet$^r$ [Bolivar, F. et al.: Gene 2, 95-113 (1977)];

pBR329 amp$^r$, chl$^r$, tet$^r$ [Covarubbias, L., Bolivar, F.: Gene, 17, 79-89 (1982)];

The $\pi$vX and AN7 plasmid DNA preparates were prepared in the Institute of Biochemistry, Biological Research Centre of the Hungarian Academy of Sciences, Szeged, Hungary [Seed, B.: Nucleic Acids Research, 11, 2427-2446 (1983)].

The employed restriction endonuclease, $T_4$ induced polynucleotide kinase and polynucleotide ligase preparates were prepared in the Institute of Biochemistry, Biological Research Centre of the Hungarian Academy of Sciences; Szeged, Hungary, using published purification methods [Roberts, R. J.: Nucleic Acids Research 11, r135-r137 (1983); Murray, N. E. et al.: J. Mol. Biol. 132, 493-505 (1979); Panet, A. et al.: Biochemistry, 12, 5045-5050 (1973)]. The Klenow fragment of enzyme DNA polymeraseI was the product of New England BioLabs, while the bacterial alkaline phosphatase (BAP) was produced by Worthington.

The [$\gamma$-$^{32}$P]ATP (Hungarian Isotope Institute, Budapest) has a specific activity of 22 TBq/mM.

The YTB culture medium [Miller, J. H., ed. Experiments in Molecular Genetics, Cold Spring Harbor Laboratory, New York (1972)] contained 10 g./lit. of Bacto Tryptone (Difco), 5 g./lit. of Bacto Yeast extract (Difco) and 5 g. of NaCl. To prepare YTA plates the YTB culture medium was supplemented with 15 g./lit. of Bacto Agar (Difco).

To isolate plasmid DNA, the bacterium strains HB101, C600 and ED8800 containing the suitable plasmids were grown on YTB culture medium containing 100 $\mu$g./ml. of ampiciliin (Pharmachim, Sofia). Before isolation of each non-pHC plasmid 170 $\mu$g./ml. of chloramphenicol were added at $OD_{600nm}$ 0.7-0.8 to the bacterium cultures which were then shaken for another 10 to 12 hours. The high copy-number (pHC) plasmids were isolated from the cells of a culture grown until stationary phase, without amplification. When isolating plasmid DNA in preparative amounts (from 50 to 100 ml. of bacterium culture in case of pHC plasmids, and from 1 to 3 lit. of culture in case of other derivatives), a clear lysate was prepared by the technique of Clewewll and Helinski [J. Bacteriol., 110, 1135 (1972)], and the plasmid DNA was purified on a Sephacryl S1000 (Pharmacia) column. To isolate plasmid DNA for analytical purposes (from 1.0 to 1.5 ml. of bacterium culture) the potassium acetate method developed by Birnboim and Doly and modified by D. Ish-Horowich was used [Maniatis, T. et al.: Molecular Cloning, Cold Spring Harbor Laboratory, New York (1982)].

The digestion of DNA samples by restriction endonucleases was performed under the reaction conditions recommended by New England BioLabs.

To transform DNA fragments with single-stranded ends to fragments with blunt ends, DNA was precipitated with alcohol after digestion with the restriction enzyme, and then dissolved in a buffer comprising 50 mM of Tris-HCl pH 7.4, 7 mM of MgCl$_2$, 1 mM of dithiothreitol, 0.1 mM of dATP, 0.1 mM of dCTP, 0.1 mM of dGTP, 0.1 mM of TTP (end volume: 10–20 μlit., DNA concentration: 200–250 μg./ml.). The solution was then incubated with 1–2 U of DNS polymeraseI Klenow fragment at 37° C., for 15 minutes [Maniatia, T. et al.: Molecular Cloning, Cold Spring Harbor Laboratory, New York (1982)].

The reaction mixture (30–40 μl.) used to ligate DNA fragments with sticky ends contained 0.5 to 1.0 μg. of DNA, 66 mM of Tris-HCl (pH 7.6), 5 mM of MgCl$_2$. 5 mM. of dithiothreitol, 1 mM of ATP and 1 U of T$_4$ induced polynucleotide ligase. Ligation was carried out at 14° C. for 2 to 3 hours [Maniatis, T. et al.: Molecular Cloning, Cold Spring Harbor Laboratory, New York (1982) ]. Fragments with blunt ends were ligated in a buffer containing 30–40 μg./ml. of DNA, 25 mM of Tris-HCl (pH 7.4), 5 mM of MgCl$_2$, 5 mM of spermidine, 1 mM of ATP, 10 μg./ml. of BSA (Sigma, Type V). To the reaction mixture 4 to 6 U of T$_4$ induced polynucleotide ligase were added, and it was incubated at 14° C. for 8 to 12 hours [Maniatis et al.: Molecular Cloning, Cold Spring Harbor Laboratory, New York (1982)].

The gel electrophoresis of DNA samples was performed in 0.8 to 2.0% agarose gels (Sigma, Type I), in horizontal electrophoresis equipments, following the technique described by Helling et al. [J. Virol. 14, 1235 (1974)]. The polyacryl amide gel electrophoresis (using 1% and 8%, 1 mm. thick, vertical gels) was performed according to Maniatis et al. [Biochemistry, 14, 3787–3794 (1975)].

To isolate DNA fragments from agarose and polyacryl amide gels the technique developed by Winberg et al. [Nucleic Acids Res. 8, 253–264 (1980)] was used, employing DEAE paper.

Competent cells for the transformation of bacterium strains HB101, C600 and ED8800 were prepared by the so-called CaCl$_2$ method reported by Mandel and Higa [J. Mol. Biol., 53, 154 (1970)].

The dephosphorylation of the 5'-ends of DNA fragments, labelling of the ends with polynucleotide kinase and [γ-$^{32}$P]ATP and determination of the nucleotide sequence were performed according to the protocol described by Maxam and Gilbert [Methods Enzymol. 65, 499 (1977)].

Of the plasmids according to the invention, the high copy-number plasmid vectors having the same replication region as pBR322, a G→T point mutation in the gene of the small RNA functioning as a repressor for replication, and (a) containing the ampicillin resistance gene of pBR322 as a selective genetical marker, and in which the gene for tetracycline resistance is lacking or inactivated, or (b) containing the genes for ampicillin and tetracycline resistance of plasmid pBR322 as a selective genetical marker, and in which the transcription of the gene for tetracycline resistance is carried out from a mutant being weaker than the natural one or from a strange promoter, are particularly preferred.

Figure 3:
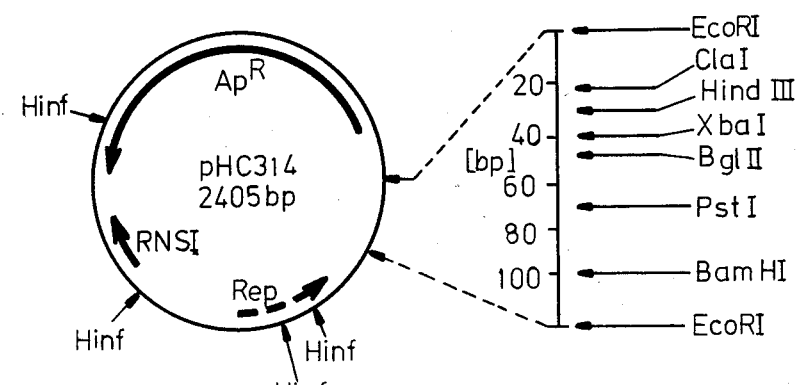
FIG. 3 is a schematic drawing of pHC314, a new plasmid vector.
Figure 4:
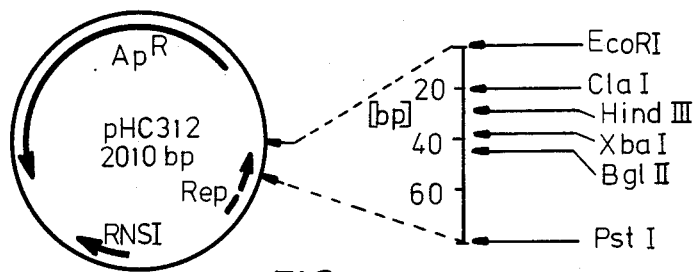
FIG. 4 is a schematic drawing of pHC312, a new plasmid vector.
Figure 5:
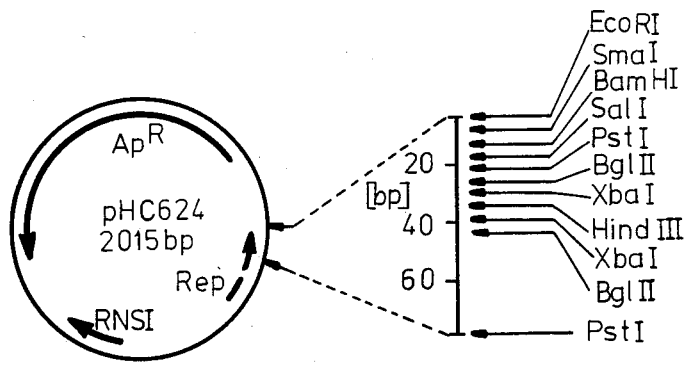
FIG. 5 is a schematic drawing of pHC624, a new plasmid vector.

The plasmids illustrated on FIGS. 3, 4 and 5 are preferred representatives of the high copy-number plasmids according to the invention, which have the following characteristic properties:

1. As a result of a modification in the structure of the gene coding for the RNA of low molecular weight functioning as a repressor of replication, their replication is derepressed, therefore the copy number inside the cell is substantially increased and generally is around 1000 (about 65% of the total DNA-content of the cell). This high copy number has no influence on the E. coli cells used as host cells.

2. The plasmids of this series contain the cleavage sites for numerous restriction endonucleases, therefore DNA fragments digested by these enzymes, by their combination or by other endonucleases producing the same ends can easily be inserted into these plasmids.

Sites suitable for cloning in the preferred plasmids according to the invention are as follows:

pHC 314: ClaI, HindIII, XbaI, BamHI, BglII and optional combinations of these sites;

pHC 312: ClaI, HindIII, XbaI, BglII, EcoRI and optional combinations of these sites;

pHC 624: EcoRI, HindIII, BamHI, XbaI, BglII, SmaI, (XmaI), SalI and their combinations with some restrictions.

3. The size of the preferred pHC plasmids is considerably smaller than that of the starting pBR322, thus the size of the plasmids illustrated on FIGS. 3, 4 and 5 is 2405 bp, 2010 bp and 2015 bp. This is advantageous since the copy number of most of the vector plasmids inside the cell is inversely proportional to the size of the plasmid. In gene cloning experiments the larger gene can efficiently be cloned when the smaller vectors are employed.

4. These plasmids have the ampicillin resistance gene of the original pBR322 as a selective genetical marker.

5. They contain the replication origo of the original pBR322.

According to another aspect of the invention there is provided a process for the preparation of high copy-number plasmid vectors, which comprises producing in the gene section, responsible for the production of the repressor for plasmid replication of a plasmid, a mutation modifying the repressor production.

According to a preferred embodiment of the process provided by the invention a point mutation modifying the repressor production is produced in the gene section coding the repressor RNA in a derivative of pBR322 or any other plasmid having the same replication region, in which the gene for tetracycline resistance is inactivated or shows repressed functioning and, if desired, the DNA section responsible for the production of membrane protein for tetracycline resistance is replaced by a synthetic polylinker DNA in one or more steps.

As hereinbefore described, the mutation preferably is a G→T point mutation in the position 3074, following the original numbering of pBR322.

There are several alternative ways available for the elimination of the problems caused by tetracycline resistance. According to a possibility, the DNA section responsible for the production of membrane protein for tetracycline resistance is replaced by a polylinker DNA of synthetic origin, which can be split by one or more important restriction enzymes. Alternatively, a foreign DNA fraction can be inserted into the gene for tetracycline resistance, which inactivates its function. According to a further possibility, the transcription of the gene for tetracycline resistance is decreased by a mutation in the promoter region or by replacing the natural promoter by a "foreign" promoter which ensures a less intensive transcription. All these techniques and their obvious modifications are within the scope of the invention.

The high copy-number plasmid vectors according to the invention have varied application possibilities, such as the preparation of any cloned section of or the whole chimaera plasmid in a pure form, for control tests, verification of structure, modification, transcloning, etc. When using the plasmids according to the invention, the same amount of DNA can be obtained from considerably less starting material than in case of the generally used plasmids known from literature. In case of the pHC plasmids exemplified, about 20–30-times less starting material is required to produce the same amount of DNA as from pBR322. The plasmid DNA, which can be isolated from a single colony of a bacterium carrying pHC plasmids, is sufficient for 3–4 restriction analyses. From one liter of bacterium culture more than 10 mg. of pure plasmid can be isolated.

If the increased amount of the product of the cloned gene is tolerable for the host cell, the synthesis of any gene product can be enhanced by using pHC plasmids according to the invention. In an optimum case the increase of yield is about 20–30-fold, since this degree of gene dose increase can be attained. In certain cases the increase will be somewhat less due to the limiting role of other factors.

The insertion of polylinker sections into the pHC plasmids gives them a high flexibility. If the cleaving sites available are not suitable for the gene to be cloned, they can be replaced or can be made suitable for cloning with other fragments by means of synthetic adapters.

As to industrial application, the production of insuline, vasopressine, etc. should be mentioned.

It is to be noted that the experiments used for the illustration of the invention are for exemplification only, and do not limit the scope of the invention. In addition to the technical solutions exemplified, there are numerous further possibilities to work the invention. For example using enzymes Fnu4HI and Tthi II, respectively, the corresponding DNA sections containing 21 and, respectively, 32 nucleotides can be cleaved from the original pBR322, the corresponding fragments containing a G→T point mutation can be synthetized chemically and inserted into the molecule of pBR322 instead of the fragments eliminated.

Similarly, a large variety of synthetic polylinker DNA fragments can be inserted into the molecule in place of the partially or entirely eliminated DNA section responsible for tetracycline resistance.

These and similar solutions and the plasmids obtained by these methods are within the scope of the invention.

Plasmids pHC 312, pHC 314 and pHC 624, respectively, were deposited in the National Collection of Microorganisms (OKI, Hungary) under Nos. 00279, 00280 and 00281, respectively, on Mar. 7, 1984.

The undermentioned microorganism strains and plasmids, respectively, were deposited in the National Collection of Microorganisms (OKI, Hungary) on July 25, 1984 under the following numbers:

*E. coli* HB 101: 00290
*E. coli* ED 8800: 00291
*E. coli* C 600: 00292
p 715: 00293
pHC 1: 00294
pHC 81: 00295
πAN7: 00296
πVX: 00297

We claim:

1. A high copy number plasmid vector containing the pBR322 origin of replication and region flanking pBR322 bp 3074, said pBR322 origin of replication located between the restriction sites for EcoRI and PvuII endonucleases, and containing:
   (a) a G→T point mutation at bp 3074, said G→T point mutation located in the region of pBR322 between bp 2978 and 3081 responsible for producing an RNA molecule which functions as a repressor of plasmid replication; and
   (b) an ampicillin resistance gene as a selective genetical marker, in said plasmid vector the tetracycline resistance gene being entirely lacking.

2. The high copy plasmid vector defined in claim 1 wherein the lacking tetracycline resistance gene is replaced by a synthetic polylinker DNA section cleavable with one or more restriction enzymes.

3. The high copy plasmid vector defined in claim 1 selected from the group consisting of pHC 314, pHC 312 and pHC 624.

4. A high copy number plasmid vector containing the pBR322 origin of replication and region flanking pBR322 bp 3074, said pBR322 origin of replication located between the restriction sites for EcoRI and PvuII endonucleases, and containing:
   (a) a G→T point mutation at bp 3074, said G→T point mutation located in the region of pBR322 between bp 2978 and 3081 responsible for producing an RNA molecule which functions as a repressor of plasmid replication; and
   (b) an ampicillin-resistance gene as a selective genetical marker, in said plasmid vector, the tetracycline resistance gene being deactivated by insertion of a foreign DNA fraction therein.

5. A high copy number plasmid vector containing the pBR322 origin of replication and region flanking pBR322 bp 3074, said pBR322 origin of replication located between the restriction sites for EcoRI and PvuII endonucleases, and containing:
   (a) a G→T point mutation at bp 3074, said G→T point mutation located in the region of pBR322 between bp 2978 and 3081 responsible for producing an RNA molecule which functions as a repressor of plasmid replication; and
   (b) an ampicillin resistance gene as a selective genetical marker, in said plasmid vector, the tetracycline resistance gene being deactivated by a mutation in its promotor region.

6. An *E coli* microorganism containing and replicating a plasmid vector according to claim 1.

7. An *E coli* microorganism containing and replicating a plasmid vector according to claim 4.

8. An *E coli* microorganism containing and replicating a plasmid vector according to claim 5.

9. A process for the preparation of a high copy number plasmid vector containing the pBR322 origin of replication and region flanking pBR322 bp 3074, said pBR322 origin of replication located between the restriction sites for EcoRI and PvuII endonucleases, which comprises the steps of:
  (a) inserting foreign DNA into a pBR322 plasmid between the EcoRI and BamHI endonuclease restriction sites to deactivate the gene for tetracycline resistance; and
  (b) mutating the pBR322 plasmid treated according to step (a) to cause a G→T point mutation at bp 3074, said G→T point mutation located in the region of pBR322 between bp 2978 and 3081 responsible for producing an RNA molecule which functions as a repressor of plasmid replication, to diminish repressor production.

10. A process for the preparation of a high copy number plasmid vector containing the pBR322 origin of replication and region flanking pBR322 bp 3074, said pBR322 origin of replication located between the restriction sites for EcoRI and PvuII endonucleases, which comprises the steps of:
  (a) decreasing transcription of the tetracycline resistance gene of pBR322 by mutating the tetracycline resistance gene promoter region; and
  (b) again mutating the pBR322 plasmid mutated according to step (a) to cause a G→T point mutation at bp 3074, said G→T point mutation located in the region of pBR322 between bp 2978 and 3081 responsible for producing an RNA molecule which functions as a repressor of plasmid replication, to diminish repressor production.

11. A process for the preparation of a high copy number plasmid vector containing the pBR322 origin of replication and region flanking pBR322 bp 3074, said pBR322 origin of replication located between the restriction sites for EcoRI and PvuII endonucleases, which comprises the steps of:
  (a) inserting foreign DNA into a pBR322 plasmid, between the EcoRI and BamHI endonuclease restriction sites to deactivate the gene for tetracycline resistance;
  (b) mutating the pBR322 plasmid treated according to step (a) to cause a G→T point mutation at bp 3074, said G→T point mutation located in the region of the pBR322 between bp 2978 and 3081 responsible for producing an RNA molecule which functions as a repressor of plasmid replication, to diminish repressor production; and
  (c) cleaving the pBR322 plasmid treated according to steps (a) and (b) with EcoRI and PvuII to form a DNA molecule with a blunt end containing the ampicillin resistance gene and thereby eliminating the tetracycline resistance gene; and
  (d) circularizing the DNA molecule formed in step (c) containing the ampicillin resistant gene with a polynucleotide ligase enzyme.

12. The process defined in claim 11 further comprising the step of inserting a DNA polylinker into the plasmid found in step (d) wherein the polylinker is inserted into the plasmid in the region where the tetracycline resistance gene has been eliminated.

* * * * *